United States Patent
Koch et al.

(10) Patent No.: US 7,371,908 B2
(45) Date of Patent: May 13, 2008

(54) PROCESS FOR CATALYTIC HYDROGENATION

(75) Inventors: Michael Koch, Speyer (DE); Ekkehard Schwab, Neustadt (DE); Peter Trübenbach, Birkenheide (DE); Harald Schäfer, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 607 days.

(21) Appl. No.: 10/267,836

(22) Filed: Oct. 10, 2002

(65) Prior Publication Data

US 2003/0073874 A1   Apr. 17, 2003

(30) Foreign Application Priority Data

Oct. 15, 2001   (DE) ............... 101 50 556

(51) Int. Cl.
*C07C 5/03*   (2006.01)
*C07C 5/08*   (2006.01)
*C07C 5/09*   (2006.01)

(52) U.S. Cl. ............ 585/266; 585/269; 585/270; 585/271; 585/273; 585/275; 585/276

(58) Field of Classification Search ........... 585/266, 585/269, 270, 271, 273, 275, 276
See application file for complete search history.

(56) References Cited

U.S. PATENT DOCUMENTS

| | | | |
|---|---|---|---|
| 3,654,129 A | | 4/1972 | Bloch |
| 3,840,608 A | * | 10/1974 | Suggitt ............... 585/267 |
| 4,155,875 A | | 5/1979 | Yamaguchi et al. |
| 4,560,817 A | * | 12/1985 | Bobsein et al. ......... 585/273 |
| 4,571,442 A | | 2/1986 | Cosyns et al. |
| 4,587,369 A | | 5/1986 | Cosyns et al. |
| 5,736,484 A | | 4/1998 | Polanek et al. |
| 5,977,423 A | * | 11/1999 | Netzer .............. 585/446 |
| 6,037,510 A | | 3/2000 | Vicari |
| 6,096,931 A | | 8/2000 | Frohning et al. |
| 6,118,034 A | | 9/2000 | Vicari et al. |
| 6,124,514 A | | 9/2000 | Emmrich et al. |

FOREIGN PATENT DOCUMENTS

| | | |
|---|---|---|
| DE | 1 067 160 | 5/1958 |
| EP | 135 442 | 3/1985 |
| EP | 151 356 | 8/1985 |
| EP | 351 186 | 1/1990 |
| EP | 792 928 | 9/1997 |
| EP | 881 275 | 12/1998 |
| EP | 922 687 | 6/1999 |
| EP | 989 106 | 3/2000 |
| EP | 994 088 | 4/2000 |
| EP | 1 205 531 | 5/2002 |
| WO | 97/32944 | 9/1997 |
| WO | 99/26905 | 6/1999 |

\* cited by examiner

*Primary Examiner*—Thuan Dinh Dang
(74) *Attorney, Agent, or Firm*—Novak Druce + Quigg LLP

(57) ABSTRACT

Hydrocarbon streams are hydrogenated catalytically without using a different solvent from the hydrocarbon stream to be hydrogenated, with a basic compound being added to the starting-material stream. The formation of undesired secondary components on the catalyst is thereby effectively prevented.

5 Claims, No Drawings

PROCESS FOR CATALYTIC HYDROGENATION

The present invention relates to a process for the catalytic hydrogenation of hydrocarbon streams. In particular, the present invention relates to a process for the catalytic hydrogenation of hydrocarbon streams without using a different solvent from the hydrocarbon stream to be hydrogenated.

In refineries and petrochemical plants, large amounts of hydrocarbon streams are produced, stored and processed. A typical process is steam cracking, in which hydrocarbons, such as naphtha, butane, gasoline or LPG ("liquefied petroleum gas") are thermally cracked, giving olefin-rich hydrocarbons. Most steam crackers are designed to maximize the ethylene and/or propylene produced, but hydrocarbons having a higher number of carbon atoms are also produced, their proportion dropping significantly with the number of carbon atoms. The constituents of the so-called "C4 cut" are usually at least partially isolated. Products having at least 5 carbon atoms, the so-called "C5$^+$ cut" (also known as "pyrolysis gasoline" in steam crackers) are usually initially not separated further. Pyrolysis gasoline tends to form a resin. The reactive alkynes, alkenynes, dienes and/or polyenes and/or alkyne, alkene, alkenyne, diene and/or polyene substituents of aromatic compounds which are responsible for this are therefore usually firstly subjected to selective catalytic hydrogenation in order to stabilize the product. A cut comprising compounds having at least six carbon atoms is subsequently obtained from the selectively hydrogenated stream, usually by distillation. This cut is subjected to further catalytic hydrogenation in order to remove all hydrogenatable compounds, with the exception of the aromatic ring structures ("aromatic nuclei") of aromatic compounds present therein. (This second hydrogenation step, in spite of the production of hydrogenatable aromatics, is frequently known colloquially as "full hydrogenation", alternatively "refining".) In full hydrogenation, which is usually carried out in the gas phase, alkenes are also hydrogenated and/or compounds containing heteroatoms, such as sulfur, nitrogen and/or oxygen, are subjected to reductive cleavage at the same time as residual alkynes, alkenynes, dienes and/or polyenes and/or alkyne, alkene, alkenyne, diene and/or polyene substituents of aromatic compounds, and thus the hydrocarbon stream is also purified of impurities containing heteroatoms, but without the aromatic products of value being hydrogenated to a significant extent. The hydrocarbon stream obtained in this way is typically subjected to extractive distillation in order to isolate the aromatics present therein, in particular benzene, toluene and/or xylene. The other constituents of the original pyrolysis gasoline are used in other ways, for example as carburetor fuel or through recycling into the steam cracker. DE 1 067 160 discloses a process for the catalytic gas-phase hydrogenation of selectively hydrogenated pyrrolysis gasoline (referred to as "refining"). In this process, the selectively hydrogenated pyrolysis gasoline is, in addition to the actual gas-phase hydrogenation, subjected to a further prehydrogenation step in the liquid phase, i.e. the full hydrogenation is split over a prereactor and a main reactor.

Another typical process is reforming. In this, hydrocarbon streams essentially consisting of alkanes and/or cycloalkanes are converted into hydrocarbons having a higher aromatic content. Like pyrolysis gasoline, but to a lesser extent, this so-called reformed gasoline comprises reactive alkynes, alkenynes, dienes and/or polyenes, and consequently the reductive removal of these impurities is usually carried out in a single hydrogenation step. EP-A-792 928 (US equivalent U.S. Pat. No. 6,124,514) describes a process for the extraction of benzene from reformed gasoline which has previously been subjected to hydrogenation on nickel or palladium catalysts on aluminum oxide supports. WO-A-97/32944 (US equivalent U.S. Pat. No. 6,118,034) teaches a process for the hydrogenation of reformed gasoline which can be carried out subsequent to aromatics extraction. According to the teaching of WO-A-97/32944, the nickel catalyst disclosed in EP-A-672 452 (US equivalent U.S. Pat. No. 5,736,484), which, according to the teaching of EP-A-672 452, is employed under different process conditions for the hydrogenation of aromatic compounds in white oils, is preferably employed for the hydrogenation of unsaturated undesired components in aromatic streams to give the aromatics.

A further source of hydrocarbon streams containing aromatic compounds is coking plants, in particular so-called crude coking-oven benzene. The products of so-called catalytic cracking (usually the FCC process, "fluid catalytic cracking") or the sulfurization of solid fuels are likewise aromatics-containing hydrocarbon streams. A feature which all these processes have in common with the processing of pyrolysis or reformed gasoline is that the aromatic compounds ultimately to be isolated as valuable products are mixed with undesired hydrogenatable impurities, in general alkynes, alkenes, alkenynes, dienes, polyenes and/or aromatics which are substituted by alkyne, alkene, alkenyne, diene and/or polyene radicals and/or compounds containing heteroatoms, such as sulfur, nitrogen and/or oxygen. As in the case of pyrolysis and reformed gasoline, these impurities are usually removed from these hydrocarbon streams by catalytic hydrogenation before the aromatic valuable products are isolated.

An example of a process in which the valuable product is not an aromatic compound is the oligomerization of low-molecular-weight alkenes, for example the di/trimerization of C4 compounds, such as isobutene, to the mixture, usually known as "isooctene", of diisobutylene, usually relatively small proportions of triisobutylene and usually relatively large proportions of the corresponding saturated hydrocarbons, and the subsequent catalytic hydrogenation of the oligomers, in the case of isooctene to give the corresponding mixture of fully saturated hydrocarbons, which is usually referred to as "isooctane". Oligomers of this type are valuable components of motor fuels owing to their high research and motor octane numbers. Thus, EP-A-989 106 discloses an integrated process for the preparation of saturated oligomers by oligomerization of short-chain olefins followed by hydrogenation. WO-A-99/26905 and EP-A-994 088 teach similar processes for the preparation of saturated dimers or oligomers. EP-A-881 275 (US equivalent U.S. Pat. No. 6,037,510) describes a process for the catalytic hydrogenation of isooctene to isooctane.

EP-A-922 687 (US equivalent U.S. Pat. No. 6,096,931) discloses a process for the catalytic gas-phase hydrogenation of aldehydes to alcohols in which nitrogen-containing bases are added to the aldehyde to be hydrogenated in order to prevent the formation of by-products, such as alkanes (by decarbonylation), ethers and/or esters from the aldehydes.

EP-A-135 442 (US equivalent U.S. Pat. No. 4,571,442) teaches a process for the hydrogenation of acetylene in a C2 cut on a palladium catalyst in which the hydrogenation is carried out in a solvent in the presence of an amine. After the hydrogenation, the C2 cut is separated from the solvent, and the latter is recycled into the reactor. EP-A-151 356 (US equivalent U.S. Pat. No. 4,587,369) teaches a similar process for the hydrogenation of a C4 cut using an amine-containing solvent. However, the removal, purification and recycling of a solvent is complex and economically disadvantageous.

Catalytic hydrogenations of this type are carried out in the gas phase, in the mixed gas-liquid phase or in the liquid phase. When carried out in the gas phase, any non-volatile components are automatically removed during the evaporation upstream of the catalyst reactor and cannot form deposits on the catalysts. However, a high-boiling or non-volatile mixture of oligomers and polymers of these compounds always forms to a certain extent in hydrogenations of this type from the reactive compounds to be hydrogenated. This mixture deposits on the catalyst and in downstream plant parts; its formation is therefore undesired and should be minimized. In the case of hydrogenations in the presence of the liquid phase, deposition of this type is not observed on the catalyst or in the reactor since oligomers and polymers formed dissolve in the liquid and are thus washed off the catalyst and plant parts and are removed. Although the extent to which these high-boiling or non-volatile constituents of the reaction product interfere with the downstream process depends on this downstream process, the lowest possible oligomer and/or polymer content is, however, generally always aimed at. In some cases, cracking reactions on the catalyst may also result in the formation of undesired cracking products, which—if they do not also have other undesired properties—at least result in a reduction in yield.

It is an object of the present invention to find a process for the catalytic hydrogenation of hydrocarbon streams in which the fewest possible undesired secondary components, such as oligomers and/or polymers and/or cracking products, are formed.

We have found that this object is achieved by a process for the catalyst hydrogenation of hydrocarbon streams without using a different solvent from the hydrocarbon stream to be hydrogenated, which comprises adding a basic compound to the starting-material stream.

By means of the process according to the invention, the formation of undesired secondary components is substantially avoided without a drop in selectivity of the catalyst being observed. The catalyst service lives in gas-phase hydrogenations are considerably lengthened, and in liquid-phase hydrogenations no problems caused by high-boiling components or non-volatile substances occur in downstream processes, or they are considerably reduced. The process according to the invention nevertheless does not have other disadvantages of known processes, such as the cost associated with the removal, work-up and recycling of solvents. In addition, it has been found that in the processes in which a loss of hydrogenatable valuable products, for example aromatics, can occur due to poor selectivity for the hydrogenation of the components to be hydrogenated which are undesired in the valuable-product stream, this loss of valuable product is significantly reduced by means of the process according to the invention.

In the process according to the invention, a basic compound is added to the starting-material stream. Typical basic compounds which are used in accordance with the invention are amines. Examples of amines used in accordance with the invention are ammonia, primary amines $RNH_2$, where R is an organic radical, for example an alkyl or aryl radical, such as methyl, ethyl, n-propyl, isopropyl, n-butyl, sec-butyl, isobutyl, tert-butyl, phenyl or benzyl, secondary amines RR'NH, where R and R', independently of one another, are an organic radical as defined for R, and tertiary amines RR'R"N, where R, R' and R", independently of one another, are an organic radical as defined for R. R and R' may also together be a cyclic radical, for example a chain of methylene groups or an aromatic ring, as in pyridine, and R, R' and R" may also together be a bicyclic radical.

Examples of suitable secondary amines are dimethylamine and morpholine.

The radicals R, R' and R" may also contain heteroatoms or may themselves be substituted, as, for example, in the amides N-formylmorpholine or N-methylpyrrolidone, or in sulfonamides.

Preference is given to the use of ammonia or a tertiary amine. Of the tertiary amines, preference is given to the trialkylamines, and of these to trimethylamine and triethylamine. Particular preference is given to the use of triethylamine.

The basic compound is added to the starting-material stream. This can be carried out upstream of the catalyst bed, at one or more feed points, or also at least partially at one or more points in the catalyst bed. The basic compound is added in the gaseous or liquid state, but can also be added dissolved in a solvent, for example water, methanol, or the starting material or product of the process according to the invention (so long as the amount of the solvent which is different from the starting material in the total starting-material stream is not significant).

The basic compound is added in an amount which is sufficient in order to achieve the desired effect of reduction of the formation of undesired secondary components, but is not so great that it interferes during further processing of the hydrogenated product. This is dependent on the type of further processing and can easily be determined in a few routine experiments. In general, the basic compound is added in an amount of at least 0.1 ppm by weight, in each case based on the total starting-material stream, preferably in an amount of at least 1 ppm by weight and particularly preferably in an amount of at least 2 ppm by weight, for example also in an amount of at least 10 ppm by weight. The added amount of basic compound is furthermore generally at most 10,000 ppm by weight, preferably at most 1000 ppm by weight and particularly preferably at most 100 ppm by weight.

By means of the process according to the invention, unsaturated hydrocarbons are hydrogenated to more highly saturated hydrocarbons and/or compounds containing heteroatoms are subjected to reductive cleavage. In particular, alkynes, alkenynes, dienes and/or polyenes and/or the alkyne, alkene, alkenyne, diene and/or polyene substituents of aromatic compounds are hydrogenated and/or compounds containing heteroatoms are subjected to reductive cleavage. It is in principle also possible to hydrogenate aromatic compounds to cycloalkanes by the process according to the invention. The hydrocarbon streams treated by means of the process according to the invention may also have already been subjected to selective or another type of incomplete hydrogenation (i.e. not every hydrogenatable bond is hydrogenated).

An important area of application of the process according to the invention is the hydrogenation of alkynes, alkenes, alkenynes, dienes and/or polyenes and/or of alkyne, alkene, alkenyne, diene and/or polyene substituents of aromatic compounds in an aromatic-containing hydrocarbon stream with simultaneous reductive cleavage of the impurities containing heteroatoms that are present in this hydrocarbon stream if such impurities are present.

Aromatics-containing hydrocarbon streams which are subjected to the process according to the invention are, in particular, (optionally selectively prehydrogenated) pyrolysis gasoline, reformed gasoline and crude coke-oven benzene.

A further important area of application of the process according to the invention is the hydrogenation of unsaturated dimers and/or oligomers produced by dimerization of alkenes. The most important example of hydrogenation of this type in industry is the hydrogenation of isooctene, which is obtained by dimerization of butenes, in particular isobutene, to isooctane.

Hydrogenation processes of this type are well known—without the addition according to the invention of a basic compound. The choice of the way in which the process according to the invention is carried out (gas phase, mixed gas/liquid phase, liquid phase) and the choice of hydrogenation parameters (recycling, temperatures, pressures, space velocities and other parameters) is a routine task for the person skilled in the art and is carried out, depending on the hydrogenation task, as generally conventional in hydrogenation processes of this type.

Typical process parameters for liquid-phase processes are a pressure in the range from 1 to 20 bar, a temperature in the range from 20 to 200° C., a space velocity ("WHSV") in liquid-phase processes in the range from 1 to 10 kg of starting-material stream per liter of catalyst and per hour and in gas-phase processes in the range from 0.3 to 5 kg of starting-material stream per liter of catalyst and per hour, a molar ratio of hydrogen to the bonds to be hydrogenated in the range from 1 to 100, and a return ratio (product recycled upstream of the reactor to fresh starting material fed to the reactor for the first time) in the range from 0 to 50.

It is possible for a slight reduction in the conversion per passage through the reactor to occur in the process according to the invention compared with a corresponding known process carried out in an identical manner with the exception of the addition of amine. This can be compensated for, if necessary, by known measures for increasing the conversion, in particular by increasing the temperature, increasing the return ratio or reducing the reactor throughput in another way, or use of somewhat larger catalyst volumes. In general, the disadvantage of reduced conversion, if it occurs, is compensated for or more than compensated for in economic terms by the reduction in the formation of undesired high-boiling or non-volatile compounds and usually also by the higher hydrogenation selectivity achieved by means of the process according to the invention.

Any hydrogenation catalyst which is known for the hydrogenation of hydrocarbon streams can be used in the process according to the invention. In general, these catalysts contain at least one element from groups 9 (cobalt, rhodium and iridium) and 10 (nickel, palladium and platinum) of the Periodic Table of the Elements and optionally also an element from group 6 (chromium, molybdenum and tungsten) of the Periodic Table of the Elements on a catalyst support.

The catalyst support is generally a conventional oxidic catalyst support, for example silicon dioxide, aluminum oxide, zirconium dioxide or a mixture of these oxides.

A suitable catalyst comprises, for example, palladium and/or platinum on aluminum oxide. More preferably, however, use is made of a catalyst which comprises nickel and/or cobalt on a catalyst support. This catalyst optionally also comprises molybdenum. In a particularly preferred manner, the catalyst used in the process according to the invention comprises nickel or nickel and molybdenum or cobalt and molybdenum, in each case on a catalyst support. The hydrogenation of reformate streams or unsaturated alkene dimers or oligomers is usually carried out using a nickel-containing catalyst, while the full hydrogenation of pyrolysis gasoline or crude coke-oven benzene is carried out using a catalyst containing cobalt and molybdenum or containing nickel and molybdenum.

Catalysts of this type are known and are commercially available. For example, catalysts of this type are available from BASF Aktiengesellschaft, Ludwigshafen, Germany, under the name "H0-22" (palladium on catalyst support), "H1-89" (nickel on catalyst supports), "M8-12" (cobalt/molybdenum on catalyst supports) or "M8-21" (nickel/molybdenum on catalyst support). The catalyst disclosed in EP-A-672 452 is likewise suitable for the process according to the invention.

EXAMPLES

The gas-phase hydrogenation experiments were carried out in a continuously operated fixed-bed reactor (50 ml catalyst volume) with gas circulation. The starting-material stream and optionally the amine were metered into the reactor with the aid of an HPLC pump via a preheater. The hydrogenated product was separated off in a separator and freed from hydrogen sulfide formed by reductive cleavage of sulfur compounds present via a scrubbing tower filled with sodium hydroxide solution.

The liquid-phase hydrogenation experiments were carried out in a continuously operated fixed-bed reactor (50 ml catalyst volume) by the trickle procedure without recycling of hydrogenated product before the reactor. The hydrogenated product was separated off in a separator.

Example 1

Hydrogenation of a Reformed Gasoline in the Liquid Phase with Addition of Triethylamine A reformed gasoline (about 35% by weight of benzene, 3% by weight of olefins and 300 ppm by weight of MCPD (acronym for methylcyclopentadiene)) was hydrogenated at 60° C., a pressure of 4 bar, a WHSV of 6 kg of starting material/liter of catalyst and per hour and a ratio of hydrogen to the total of olefins and diolefins of 3 mol/mol on a supported nickel catalyst prepared in accordance with Example 1 of EP-A-672 452. The hydrogenation was initially carried out without metering-in of amine until the steady state was reached, which in this experiment was the case after an operating time of 220 hours. 300 ppm by weight of triethylamine were subsequently added over the course of 300 hours, then 10 ppm of triethylamine were subsequently added over a further operating time of 300 hours, and 2 ppm of triethylamine were added over the subsequent 100 hours of operating time until a steady state was reached. In this experiment, this steady state was reached after a total experimental time of 900 hours, calculated from the beginning of the experiment.

The results determined in each case in the steady state are compared in Table 1.

The following table shows the run time calculated from the beginning of the experiment until the respective steady state was reached at the top of the columns in question.

TABLE 1

|  | Without amine (220 h) | With amine (900 h) |
|---|---|---|
| MCPD conversion [mol %] | 100 | 100 |
| Olefin conversion [mol %] | 99.9 | 92 |
| Benzene conversion [mol %] | 6.4 | <0.2 |
| Oligomers [ppm by wt.] | 32 | <5 |

The comparison in Table 1 shows that in the process according to the invention, compared with conventional procedures, the undesired loss of valuable product due to benzene hydrogenation and the formation of oligomers drop significantly with an only slightly lower olefin conversion.

Example 2

Hydrogenation of a Reformed Gasoline in the Liquid Phase with Addition of Trimethylamine Example 1 was repeated, but a reformed gasoline containing about 60% by weight of benzene, 2% by weight of olefins and 500 ppm by weight of MCPD was used, and trimethylamine was added instead of triethylamine.

The results determined in each case in the steady state are compared in Table 2.

TABLE 2

|  | Without amine (120 h) | With amine (750 h) |
|---|---|---|
| MCPD conversion [mol %] | 100 | 100 |
| Olefin conversion [mol %] | 99.9 | 94 |
| Benzene conversion [mol %] | 7.4 | 0.6 |
| Oligomers [ppm by wt.] | 40 | <5 |

The comparison in Table 2 shows that in the process according to the invention, compared with conventional procedures, the undesired loss of valuable product due to benzene hydrogenation and the formation of oligomers are significantly reduced with only slightly lower olefin conversion.

Example 3

Hydrogenation of a Reformed Gasoline in the Liquid Phase with Addition of Ammonia Example 1 was repeated, but a reformed gasoline comprising about 40% by weight of benzene, 3% by weight of olefins and 500 ppm by weight of MCPD was used, and 100 ppm by weight of ammonia were added instead of triethylamine without metering-in of amine after the steady state had been reached.

The results determined in each case in the steady state are compared with Table 3.

TABLE 3

|  | Without amine (190 h) | With amine (310 h) |
|---|---|---|
| MCPD conversion [mol %] | 100 | 70 |
| Olefin conversion [mol %] | 99.8 | 20 |
| Benzene conversion [mol %] | 5.2 | 0 |
| Oligomers [ppm by wt.] | 80 | 20 |

The comparison in Table 3 shows that in the process according to the invention, compared with the conventional procedure, the undesired loss of valuable product due to benzene hydrogenation and the formation of oligomers drop significantly, but the use of ammonia also results in a greater drop in yield compared with other amines.

Example 4

Full Hydrogenation of a Selectively Free-Hydrogenated Pyrolysis Gasoline in the Gas Phase with Addition of Triethylamine A selectively prehydrogenated pyrolysis gasoline (about 35% by weight of benzene, 20% by weight of toluene, 8% by weight of xylenes, bromine number (ASTM D1159) 27 g/100 g and 300 ppm of sulfur (as a constituent of sulfur compounds)) was hydrogenated at 320° C., a pressure of 30 bar, a WHSV of 1.6 kg of starting material/liter of catalyst and per hour, a ratio of circulating gas to starting material fed to the reactor for the first time of 400 l (s.t.p.)/kg (1 (s.t.p.) of circulating gas per kg of fresh starting material; 1 (s.t.p.)="liters at standard temperature and pressure", volume at a pressure of 1 bar abs. and a temperature of 0° C.) on a commercially available cobalt/molybdenum catalyst on aluminum oxide support (catalyst M8-12 from BASF Aktiengesellschaft, 14.5% by weight of $MoO_3$, 3.4% by weight of CoO, BET surface area 240 $m^2$/g, in the form of pellets having a diameter of 2.5 mm), until the steady state was reached. 100 ppm by weight of triethylamine were subsequently added until the steady state was reached again.

The results determined in each case in the steady state are compared in Table 4.

TABLE 4

|  | Without amine (120 h) | With amine (320 h) |
|---|---|---|
| Bromine number [g/100 g] | 0.5 | 0.5 |
| Sulfur [ppm] | 2 | 1 |
| Benzene conversion [mol %] | 0.7 | 0.66 |
| Cyclohexylbenzene [ppm by wt.] | 140 | 60 |
| High boilers[1] [ppm by wt.] | 1500 | 1000 |

[1]"high boilers" are compounds having a retention time of 74-100 min during recording of a gas chromatogram using a Petrocol column The comparison in Table 4 shows that in the process according to the invention, compared with the conventional procedure, the undesired loss of valuable product due to benzene hydrogenation and the formation of oligomers dropped significantly with an identical olefin conversion (same bromine number).

Example 5

Hydrogenation of an Isooctene in the Gas Phase with Addition of Triethylamine

An isooctene mixture (34.2% by weight of diisobutylene, 3.8% by weight of triisobutylene, 62% by weight of isooctane and 52% by weight of thiophene (corresponds to 20% by weight of sulfur)) was hydrogenated at a pressure of 22 bar, a WHSV of 2.8 kg of starting material/liter of catalyst and per hour (in this case corresponds to a WHSV of 1.1 kg of olefin fraction in the starting material stream/liter of catalyst and per hour) and a ratio of circulating gas to starting material fed to the reactor for the first time of 3200 l (s.t.p.)/kg on a commercially available cobalt/molybdenum catalyst on aluminum oxide support (catalyst M8-12 from BASF Aktiengesellschaft, 14.5% by weight of $MoO_3$, 3.4% by weight of CoO, BET surface area 240 $m^2/g$, in the form of pellets having a diameter of 2.5 mm) at 270° C. until the steady state was reached. The temperature was then lowered to 250° C., and the steady state was again awaited. 100 ppm by weight of triethylamine were subsequently added under otherwise constant conditions until the steady state was again reached, and the temperature was subsequently increased to 270° C. under otherwise constant conditions, again until the steady state was reached.

The results determined in each case in the steady state are compared in Table 5.

TABLE 5

|  | Without amine | | With amine | |
| --- | --- | --- | --- | --- |
|  | 270° C. (70 h) | 250° C. (170 h) | 250° C. (370 h) | 270° C. (470 h) |
| Olefin conversion [mol %] | 99.1 | 99.0 | 97.2 | 98.9 |
| Selectivity C8+ [mol %] | 97.0 | 97.6 | 99.3 | 98.6 |
| Bromine number [g/100 g] | 0.2 | 0.8 | 1.9 | 0.4 |
| Sulfur [ppm by wt.] | 1 | 1 | <1 | <1 |

The comparison in Table 5 shows that in the process according to the invention, compared with the conventional procedure, the selectivity of the hydrogenation increases with an only slightly lower olefin conversion.

We claim:

1. A process for the catalytic hydrogenation of hydrocarbon streams, comprising hydrogenating hydrocarbon starting-material streams, selected from the group consisting of pyrolysis gasoline, reformed gasoline, and crude coke-oven benzene to remove all hydrogenatable compounds, with the exception of the aromatic ring structure of aromatic compounds present therein, without using a different solvent from the hydrocarbon stream to be hydrogenated, which comprises adding an amine to the starting-material stream.

2. A process as claimed in claim 1, wherein a trialkylamine is added.

3. A process as claimed in claim 1, wherein the pyrolysis gasoline is selectively prehydrogenated.

4. A process as claimed in claim 1, wherein use is made of a catalyst which comprises at least one element from groups 9 and 10 of the Periodic Table of the Elements and optionally also an element from group 6 of the Periodic Table of the Elements on a catalyst support.

5. A process as claimed in claim 3, wherein use is made of a catalyst containing nickel or cobalt, and optionally also molybdenum, on a silicon dioxide, zirconium dioxide and/or aluminum oxide catalyst support.

* * * * *